(12) United States Patent
Haasse et al.

(10) Patent No.: US 8,088,358 B2
(45) Date of Patent: Jan. 3, 2012

(54) PARAMAGNETIC NANOPARTICLE

(75) Inventors: Markus Haasse, Hamburg (DE);
Stephan Haubold, Hamburg (DE);
Cornelius Bobbert, Wartenberg (DE);
Beate Stoeckelhuber, Lubeck (DE)

(73) Assignee: Centrum fur Angewandte Nanotechnologie (CAN) GmbH, Hamburg (DE)

( * ) Notice: Subject to any disclaimer, the term of this patent is extended or adjusted under 35 U.S.C. 154(b) by 305 days.

(21) Appl. No.: 10/471,302

(22) PCT Filed: Mar. 4, 2002

(86) PCT No.: PCT/DE02/00772
§ 371 (c)(1),
(2), (4) Date: Jan. 29, 2004

(87) PCT Pub. No.: WO02/072154
PCT Pub. Date: Sep. 19, 2002

(65) Prior Publication Data
US 2004/0156784 A1 Aug. 12, 2004

(30) Foreign Application Priority Data

Mar. 8, 2001 (DE) .................................. 101 11 321

(51) Int. Cl.
*A61B 5/055* (2006.01)
*A61K 49/00* (2006.01)
(52) U.S. Cl. ........................................ 424/9.1; 424/9.32
(58) Field of Classification Search .................. 424/9.32
See application file for complete search history.

(56) References Cited

U.S. PATENT DOCUMENTS

| | | | | |
|---|---|---|---|---|
| 4,998,065 A | | 3/1991 | Koizumi | 324/309 |
| 5,078,994 A | * | 1/1992 | Nair et al. | 424/501 |
| 5,122,363 A | * | 6/1992 | Balkus et al. | 424/9.31 |
| 5,456,986 A | | 10/1995 | Majetich et al. | 428/403 |
| 5,496,536 A | | 3/1996 | Wolf | |
| 5,670,480 A | * | 9/1997 | Hogan, Jr. | 514/12 |
| 5,725,800 A | * | 3/1998 | Huguenin | 252/301.4 P |
| 6,048,515 A | | 4/2000 | Lawaczek et al. | |
| 6,530,944 B2 | * | 3/2003 | West et al. | 607/88 |
| 6,699,406 B2 | * | 3/2004 | Riman et al. | 252/301.36 |
| 2003/0032192 A1 | * | 2/2003 | Haubold et al. | 436/56 |

FOREIGN PATENT DOCUMENTS

| | | |
|---|---|---|
| DE | 199 54 960 | 6/2000 |
| WO | WO 00/50504 | 8/2000 |
| WO | WO 00/56837 | 9/2000 |
| WO | WO 02/20696 | 3/2002 |

OTHER PUBLICATIONS

Coroiu (Journal of Magnetism and Magnetic Materials 1999, 201, 449-452).*
Riwotzki et al. (J. Phys. Chem. B 2000, 104, 2824-2828).*
Oliveira et al. (J. Alloys and Compounds 2000, 303-304, 157-161).*
K. Riwotzki et al., "Liquid Phase Synthesis of Doped Nanoparticles; Colloids of Luminescing $LaPO_4$:Eu and $CePO_4$:Tb Particles with a Narrow Particle Size Distribution", J. Phys. Chem. B2000, 104, 2824-2828.
M. Haase et al., "Synthesis and properties of colloidal lanthanide-doped nanocrystals", Journal of Alloys and Compounds 303-304 (2000) 191-197.
H. Meyssamy et al., "Wet-Chemical Synthesis of Doped Colloidal Nanomaterials: Particles and Fibers of $LaPO_4$:Eu, $LaPO_4$:Ce, and $LaPO_4$:Ce,Tb", Advanced Materials, 1999, 11 No. 10, 840-844.
S. Anderson, et al., "Magnetic Resonance Contrast Enhancement of Neovasculature With $\alpha_v\beta_3$—Targeted Nanoparticles", Magnetic Resonance in Medicine 44:433-439 (2000).
Coroiu, I. "Relaxivities of different superparamagnetic particles for application in NMR tomography" *Journal of Magnetism and Magnetic Materials*, 201:449-452 (1999).
Neogy, D., et al. "Experimental and theoretical studies on the magnetic behavior of $Nd^{3+}$ in $NdPO_4$" *Journal of Magnetism and Magnetic Materials*, 173:167-172 (1997).
Morel S et al: "NMR" relaxometric investigations of solid lipid nanoparaticles (SLN) containing gadolinium (III) complexes European Journal of Pharmaceutics and Biopharmaceutics,Elsevier Science Publishers B.V., Amsterdam, NL, vol. 45, No. 2, Mar. 1998, pp. 157-163, p. 158, right-hand column, paragraph 3, p. 162, left-hand column, paragraph 3, p. 159, left-hand column, paragraph 2.
Bulte J W M et al: "Magnetic Nanoparticles As Contrast Agents for MR Imaging" Scientific and Clinical Applications of Magnetic Carriers, XX, XX,—1997, p. 527-543, figure 4; table 1.
Tokumitsu H et al: Gadolinium Meutron-Capture Therapy Using Novel Gadopentetic Acid-Chitosan Complex Nanoparticles: in Vivo Growth Suppression of Experimental Melanoma Solid Tumor Cancer Letters, New York, NY, US, 2000, vol. 150, No. 2, 2000, pp. 177-182, p. 178, left-hand column, paragraph 4, p. 179, left-hand column, paragraph 1.
Database Medline Online! Dec. 2000, Yu X et al: "High-resolution MRI characterization of human thrombus using a novel fibrin-targeted paramagnetic nanoparticle contrast agent." (Database accession No. NLM11108623) Abstract.
Magnetic Resonance in Medicine: Official Journal of the Society of Magnetic Resonance in Medicine / Society of Magnetic Resonance in Medicine. United States Dec. 2000, vol. 44, No. 6, Dec. 2000, pp. 867-872.
International Search Report, 2002.

* cited by examiner

*Primary Examiner* — Michael G Hartley
*Assistant Examiner* — Melissa Perreira
(74) *Attorney, Agent, or Firm* — Scully, Scott, Murphy & Presser, P.C.

(57) ABSTRACT

The present invention relates to the preparation and use of nanoparticles, in particular paramagnetic nanoparticles, and their use as contrast enhancers for NMR-based methods of examination. A significant increase in contrast (e.g. from 100 to 200%) takes place according to the invention. An aqueous or organic synthesis leads to small nanoparticles which have a narrow size distribution and can also be advantageously used for many other industrial applications.

19 Claims, 1 Drawing Sheet

PARAMAGNETIC NANOPARTICLE

PRIOR ART

Figure 1:
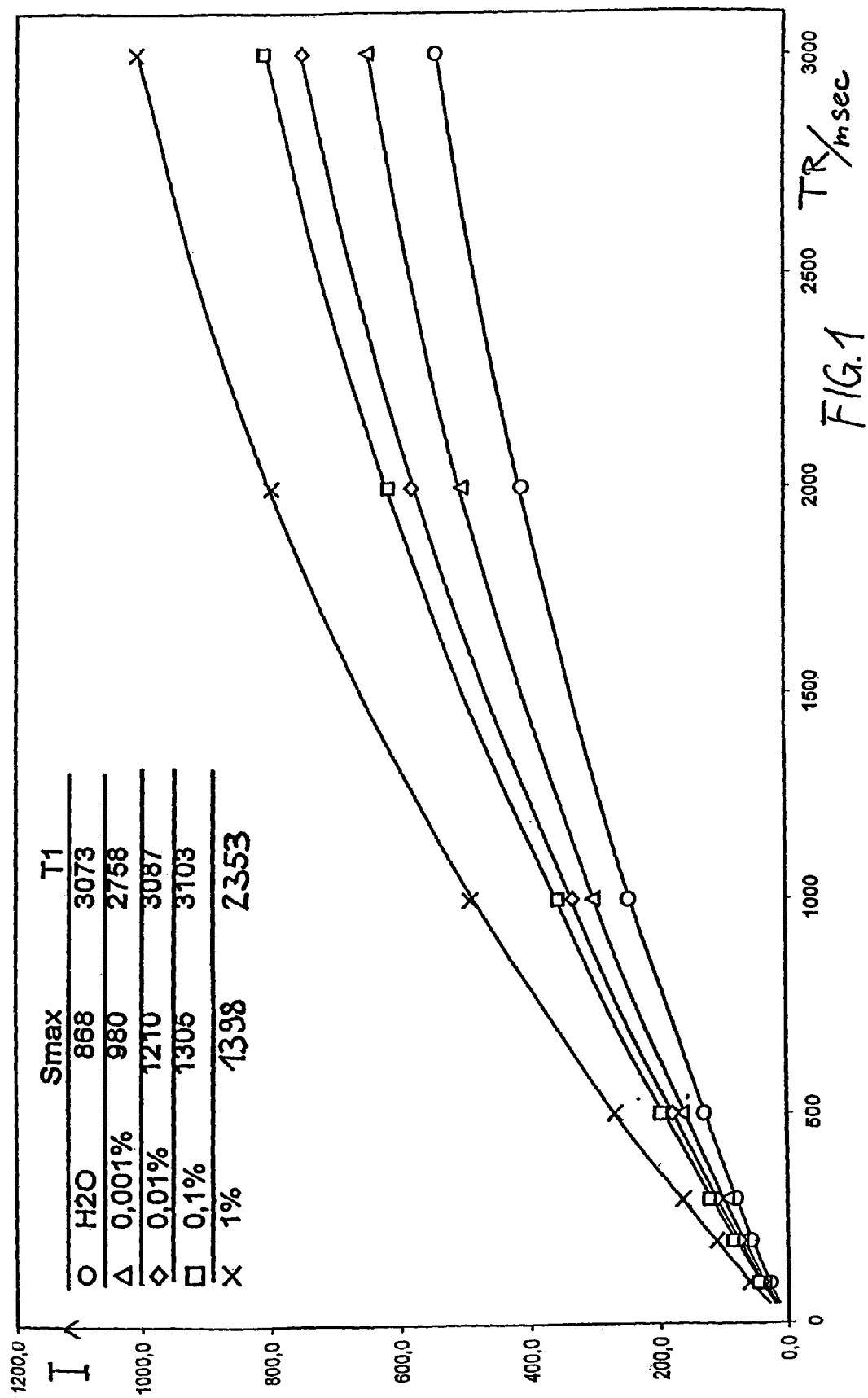

The present invention relates generally to the improved preparation of nanoparticles and in particular to the use of paramagnetic nanoparticles as contrast enhancers for NMR-based methods of examination.

Nanoparticles cannot yet be prepared efficiently in narrowly defined ranges of small size, for instance a few nanometers, e.g. 4 nm, by preparative methods of the prior art. However, this would be desirable for many industrial applications. This general object is achieved by the present invention.

Although the present invention has a wide scope both in respect of the range of materials claimed and in respect of the many considerable applications, it will in the following be contrasted from the prior art using a specific area of prior art as an example. This area of prior art is the field of nuclear magnetic resonance, known as NMR.

This technique is used as test method especially in diagnostic medicine, but also in materials research and testing.

In terms of its practical application, NMR is notable as a method of noninvasive examination. The method is based on determining the different distribution of hydrogen atoms from tissue to tissue and is employed in medicine as MRT (Magnetic Resonance Tomography). A brief introduction to the subject may be found in: "Schild Prof. Dr. Hans H.:MRI made easy, Schering Aktiengesellschaft, 1990. ISBN 3-921817-41-2".

An essential role in this technique is played by the element hydrogen. It possesses one proton (atomic number Z=1) and, like all elements having an odd atomic number, has a momentum in the form of intrinsic rotation of the nucleus, known as nucleus spin. This rotation generates a magnetic moment which makes the atom concerned a magnetic dipole. However, in a volume containing hydrogen atoms, the magnetic moments are aligned randomly.

If, however, an external, static magnetic field is applied, the atomic nuclei become aligned along the magnetic field lines. They are then positioned parallel or antiparallel to the axis of the external magnetic field. The atoms precess around the magnetic field lines of the main field at the Larmor frequency; most nuclei are aligned parallel (low-energy state) to the external magnetic field, while a smaller number are aligned antiparellel. There is thus a net magnetic moment in the z direction (direction of the magnetic field lines of the external field) and the components in the xy plane cancel out by vectorial addition.

If an alternating electromagnetic field (HF radiowaves) at exactly the Larmor frequency is then applied, the transfer of energy (resonance) results in a deflection of the net magnetic moment from the z direction, with the duration of the pulse of the applied alternating field and its amplitude determining the angle by which the sum vector is deflected.

When the alternating field pulse stops, the "relaxation" of the sum vector perpendicular to the xy plane, i.e. once again parallel to the z direction, leads to an alternating current which can be measured with the aid of a coil.

Here, two parameters, each expressed as time, are of particular interest: thus, the longitudinal or spin-lattice relaxation time $T1$ describes the time constant of the return of the z component of the sum vector to its original position. The transverse or spin-spin relaxation time $T2$ describes the loss of phase coherence due to field inhomogeneity and relaxation.

The relaxation time is dependant on the applied field strength and on the type of tissue. Differences in the type of tissue can be established by means of the relaxation time. Spatial resolution is achieved by applying not a homogeneous magnetic field but a gradated field. As a result, the Larmor frequency, which is proportional to the applied field, is different in each (thin) layer of the tissue to be examined and an NMR signal can therefore be assigned unambiguously to a layer of tissue.

In the field of medicine, the applications of the NMR technique have expanded from the well-known use as MRT to the following uses:

Magnetic resonance spectroscopy (MRS): this is an investigative method which also gives biochemical information. Thus, defined metabolites generate signals in this method. Their concentration can be superimposed either graphically as a spectrum or brightness-coded on morphological MRT images (cf. Thurn and Bucheler, Einführung in die radiologische Diagnostik, Thieme-Verlag, 1998).

Magnetic resonance angiography (MRA): changes in the MRT signal due to moving spin caused by blood flow lead to additional information which here forms the basis of imaging of the blood vessels.

Cardiac magnetic resonance tomography: the diagnosis of heart disease is here based not exclusively on morphological image information, but is coupled with functional analyses. This coupling results from an ECG-triggered MRT examination of the heart, and later reconstruction (for instance in the form of a three-dimensional view) enables functional weaknesses of the heart to be recognized.

MR functional imaging: an increased $T2$ is measured in activated brain regions as a result of increased blood flow and higher oxygen consumption and the signals in these regions therefore become slightly more intense in $T2$-weighted sequences. A difference image of the states with and without activity allows activated regions to be recognized.

An MRT examination generally consists of at least one $T1$-weighted series and a $T2$-weighted series. However, it has become established practice in many investigations to follow these two tests by a $T1$-weighting with addition of a contrast agent.

Contrast agents are used in about one third of MR examinations. They shorten the relaxation times $T1$ and $T2$ in tissues so that the tissue contrast is increased and both anatomy and physiological processes can thus be assessed more readily, and pathological findings can also be presented more clearly.

The mechanism by which the contrast is increased in NMR imaging with the aid of a contrast agent is based on the presence of an unpaired electron. This electron has a magnetic moment which is about 1000 times that of a proton. This magnetic moment leads to a rapid change in the local magnetic field. The dipoles of unpaired electrons have a considerably stronger magnetic susceptibility when they are located in densely packed crystalline structures. These substances are referred to as superparamagnetic and have a magnetic susceptibility which is from 100 to 1000 times that of paramagnetic substances. They have a significantly greater effect on the image contrast (shortening of $T2$) than do paramagnetic substances.

Paramagnetic substances can also be used for increasing the signal intensity. They are able to produce an increase in the signal intensity even in a low concentration. At higher concentrations, the signal strength reaches a plateau and then drops again as the concentration is increased further. This applies approximately equally to $T1$- and $T2$-weighted measurements, with the plateau described followed by a drop in the signal intensity as the contrast agent concentration increases tending to be reached earlier in the T1 measurement.

In the search for contrast agents, free ions of the transition elements ($Mn^{2+}$, $Cu^{2+}$, $Fe^{3+}$, $Cr^{3+}$ etc.) have been studied in the prior art, but further plans to use such ions quickly had to be abandoned because of their excessive toxicity in the body and their poor solubility in the region of the pH of blood (7.35-7.45).

In medical applications of NMR, gadolinium-containing contrast agents have become more widely used because of their good contrast-enhancing-capability.

However, since the gadolinium ion in the form of its chloride, sulphate or acetate is toxic and accumulates in the reticuloendothelial system (monozyte-macrophage system) and in the liver, bones and spleen, it is always employed in the form of a chelate, for instance as (diethylenetriamine) gadolinium pentaacetate (Gd-DTPA).

In the chemical structure of this compound, the gadolinium 3+ ion is located in the middle of the chelate and is relatively closely surrounded by other molecules. The gadolinium ion has a total of nine coordination sites.

In order to have a contrast-increasing action, the gadolinium ion has to bond 12 water molecules for the distance between hydrogen nuclei and the Gd ion to be small enough.

A disadvantage is the high level of shielding of the gadolinium ion from the surroundings by the chelating agent. This hinders free access of water molecules to the gadolinium ion, as is necessary for contrast enhancement. If the chelate bond is broken, there is the direct risk of liberation of the toxic gadolinium ion and damage to the organism would be likely. Natural limits are therefore placed on the "gadolinium plus complexing agent" system in respect of the contrast-enhancing action in NMR studies.

In this complexed form, gadolinium circulates purely extracellularly (blood vessels and interstitium) and can also not pass the (intact) blood-brain barrier. Penetration into the interior of cells likewise does not occur to any significant extent. This is attributed to the pronounced hydrophilicity of the compound.

Excretion occurs via glomerular filtration in the kidneys at a free form time of about 90 minutes. Tubular secretion or resorption was not observed. Gd-chelates can therefore theoretically be used as contrast agents for MRT urograms. Gd-DTPA is likewise dialyzable; removal occurs in about the same time as in the case of persons having healthy kidneys.

Bonding in the chelate is sufficiently stable, and the stability constant has been reported as $10^{22}$. A life of 5 years is guaranteed for this compound.

Gd-DTPA is commercially available, for example under the product name "Magnevist™". A description of this contrast agent in terms of its mode of action as contrast enhancer may be found in "Felix Roland, Heshiki Atsuko et.al., (Editors): 'Magnevist', Blackwell Science, 3rd Edition 1998, pp. 1 to 27." Reference may be made to this for a general understanding and for further technical details.

Gd-DTPA in free from binds calcium and magnesium, in each case in ionized form, which leads to a drastic shift in the electrolyte balance and can lead to disturbances of the heart rhythm as far as cardiac arrest.

In biochemical tests, Gd-DTPA has been found to be quite inert, and a displacement of Gd from this compound by other ions have not yet been observed. Metabolites of this compound are likewise not yet known, nor are changes of form. However, some remaining risk to the patient cannot be ruled out.

Furthermore, Gd-DTPA is very expensive for use in medical diagnostics because of the expensive complexing agent and the high purity requirements.

However, in particular situations in medical practice, it is extremely desirable to increase the contrast in imaging so that the measurement results can be presented more clearly as a basis of medical diagnosis and are therefore easier to interpret.

Furthermore, it is desirable to have available a contrast agent for oral administration in addition to arterially venous administration in medical NMR diagnostics. This is at present not economically feasible using Gd-DTPA, since the amount of contrast agent to be ingested in the case of oral administration is significantly higher than in the case of arterial/venous administration. Oral administration of Gd-DTPA is therefore too expensive.

ADVANTAGES OF THE INVENTION

Compared to the known approaches to a solution, nanoparticles as set forth in claim 1, 2 or further subsidiary claims have the advantages that they can be prepared with a narrow size distribution, viz. mean deviations of about 1 nm, and a small size, for example in the range from 2 to 15 nm, and that they do not agglomerate and are therefore very well suited to many industrial applications, not only NMR-specific applications.

In NMR-specific applications, paramagnetic nanoparticles, either prepared according to the present invention or prepared by other methods known from the prior art, have the advantages that they can provide medical MRT diagnostics with contrast-enhanced images, that they can appreciably reduce costs and that they reduce the risk to human health presented by the toxicity of the contrast agent. Risks which could be posed by free DTPA are automatically ruled out in the use according to the invention of nanoparticles without a DTPA complex. In addition, the rare earth element on which the nanoparticles are based is not present in free form but is instead built into a crystal lattice, so that no interaction with the patient's body is possible as a result of the low solubility.

Two synthetic routes, one using water and the other using an organic solvent, are presented according to the invention for the nanoparticles. They both lead to nanoparticles which have a narrow size range, do not agglomerate and are homogeneously dispersible in any carrier fluids, which is an indispensable prerequisite for many applications.

The synthesis steps are not specifically for nanoparticles having a contrast-enhancing action in NMR. It is likewise possible to achieve other physical or chemical effects, e.g. fluorescence, with appropriate doping.

According to further aspects of the present invention, the nanoparticles of the invention make it possible to achieve numerous further applications and advantages which are all based on characteristic properties of the nanoparticles of the invention.

a. their excellent nuclear resonance performance at a significantly lower usage amount than in the prior art, and
b. the ability to disperse the nanoparticles homogeneously in any material.

Thus, any liquids, for example as intermediates in the production of any article to be formed therefrom, can be admixed with nanoparticles according to the invention and later examined by NMR-based methods to detect tiny material defects such as air inclusions, etc. Such liquids will hereinafter also be referred as liquid materials.

One main aspect of the present invention is the use of paramagnetic nanoparticles for increasing the contrast or altering the relaxation time of a material or tissue to be examined. A preferred use is as MRT contrast agent in medical diagnostics.

Advantageously, the use of the nanoparticles of the invention requires no complexing agents to mask the toxicity of the contrast agent, since the contrast-enhancing substance, for example gadolinium, is built into a crystal lattice, for example GDPO4 in a monazite lattice. Despite the stable incorporation of the contrast-enhancing substance into a lattice, it is nevertheless ensured that, owing to the high proportion of surface atoms, more free coordination sites for hydrogen atoms are available than in the prior art (1/9).

For example, in the case of GDPO4 nanoparticles having a diameter of 5 nanometers, about 40% of all atoms are located on the surface. When the entire nanoparticle consists of 10 000 atoms, then there are about 4000 surface atoms. In the case of GDPO4, precisely 20% of these are gadolinium atoms. Thus, about 800 Gd atoms are available for hydrogen atoms. As the size of the nanoparticles decreases, the result becomes even better.

For the same absolute amount of NMR-enhancing substance, for example gadolinium in the form of gadolinium phosphate, there are significantly more reactive gadolinium centers on the surface of the nanoparticles of the invention than in the complexing agent of the prior art. For this reason, the dosage can be reduced when using the nanoparticles-based contrast agent of the invention, or in the case of the same dosage of material, the measurement time can be reduced.

There is also the opportunity of employing substances other than gadolinium, which may be cheaper, having an intrinsically smaller contrast-enhancing effect when the effect is increased again by incorporation in nanoparticles.

The subordinate claims describe advantageous embodiments and improvements of the respective subject matter of the invention.

In a further aspect of the present invention, metal chlorides are used in the preparative process of the invention for obtaining the cationic compound of the lattice, or a phosphate is used for obtaining its anionic component, and an acid scavenger, preferably an amine, particularly preferably trioctylamine ($C_{24}H_{51}N$), is added to the synthesis. If chloride salts are used, the yield of material, based on the amount of metal salts used, is about 80%, which makes a preparative process on an industrial scale possible. A lattice having a rare earth cation and an anionic phosphate can thus be prepared advantageously in this way.

If a phosphoric ester is used as solvent for the reaction, the growth of the nanoparticles can be controlled. The use of a phosphoric ester gives a high yield of nanoparticles having a narrow size distribution. The phosphoric ester can be used stoichiometrically in a ratio of metal chloride: phosphoric ester of 1:1 through to a ratio of 1:$\infty$.

However, the substances disclosed in the simultaneously filed PCT application PCT/DE 00/03130 having the title 'Dotierte Nanopartikel' and its continuation application, both by the same applicant, can also be used as solvents for obtaining the nanoparticles of the invention.

The nanoparticle material obtained from the process can, after precipitation and drying, for example by means of hot air, be a soft crumbly, very finely particulate powder concentrate which can then in turn be incorporated in many carriers, in particular carrier liquids or liquid materials, depending on what is required by the particular application. Thus, the nanoparticles can, in addition to being used as contrast agents, also be incorporated into any other articles, in particular articles produced by casting and other shaping processes, including films, etc.

If the melting point of the material is too high, so that the advantageous properties of the nanoparticles would be lost as a result of the high melting temperature, the nanoparticles can be firmly joined to the surface by rolling.

In the case of materials having a lower melting point, a homogeneous mixture can be produced by stirring the carrier liquid with the material and this can later be utilized for, inter alia, nondestructive testing of the material.

The nanoparticles of the invention can be synthesized in an organic medium or in an aqueous medium. Both synthetic routes are disclosed in the simultaneously filed, international application PCT/DE 00/03130 having the title 'Dotierte Nanopartikel' and its continuation application, both by the same applicant, for a large number of different nanoparticles, in particular nanoparticles having different types of doping.

Likewise, the preparative processes disclosed there can be employed for preparing undoped nanoparticles, as can easily be recognized by a person skilled in the art since doping of the nanoparticles is not essential for the targeted-size synthesis, whether in organic or aqueous medium.

The substances disclosed and/or claimed herein can also be prepared particularly advantageously using the aqueous synthesis disclosed in the simultaneously filed German patent application DE 100 58 544.2 having the title 'Phasentransfer von Nanopartikeln' by the same applicant.

The various variable starting materials make it possible to obtain, according to the invention, a wide range of materials comprising nanoparticles comprising rare earth compounds, in particular paramagnetic nanoparticles, which are preferably but not exclusively able to be prepared using the process as defined in the claims.

Depending on the chemical and physical properties, these materials can then be supplied in a targeted manner to a commercial use. NMR examinations for MRT and for nondestructive materials testing are the main applications recognizable at present for the paramagnetic nanoparticles. Further applications are those described in the abovementioned international patent application which make use of the optical (UV, VIS or NIR) properties of the nanoparticles, in particular the fluorescence properties.

When the material comprises nanoparticles in a size range from 1 to 1000 nm, preferably from 1 to 500 nm, more preferably from 1 to 100 nm, even more preferably from 1 to 20 nm and most preferably from 4 to 5 nm, with a standard deviation of less than 30%, preferably less than 10%, then the efficiency of the desired action of the nanoparticles can be increased, as has already been described above. Even very fine and uniform dispersions of the nanoparticles in other carriers or materials are thus possible. As a result, the technical effect desired in each case is utilized in an economically efficient manner. When the material, in particular one used as contrast agent, comprises a phosphate compound, it has the advantage of being relatively simple to prepare and having a low toxicity.

Owing to their good action as contrast enhancers, the contrast agents comprising gadolinium phosphate nanoparticles are particularly useful for the medical NMR application. However, neodymium phosphate and europium phosphate nanoparticles are also suitable.

The nanoparticles of the invention are likewise suitable as antibody markers for NMR tests carried out in vitro. Likewise, cancer and inflammation cells can be marked by methods of the prior art for the purposes of histology. Here, very thin layers of tissue taken from the patient are treated. In the prior art, this has hitherto only been possible by means of fluorescent nanoparticles as markers. According to the invention, the antibody detection method could be modified analogously using NMR-sensitive nanoparticles.

Further applications are: use of the nanoparticles of the invention as MRT contrast agents for in-vivo examination to detect antibodies by coupling of the nanoparticles to these. Furthermore, the nanoparticles of the invention are suitable as NMR and MRT antibody markers at the same time.

The nanoparticles of the invention are suitable as NMR and MRT antibody markers in vitro and as MRT antibody markers in vivo. The additional NMR analysis capability gives better properties as a diagnostic aid with a view to a more precise measurement results than can be achieved using fluorescence. The ability to be used simultaneously in vivo and in vitro saves the manufacturer of the antibodies the costs of developing an antibody for the other application.

If the nanoparticles prepared according to the invention are introduced into a carrier liquid, a prescribed aliquot can be diluted and dispersed in another medium such as rubber, polymers, etc.

This then forms the basis of the use according to the invention of this liquid for producing moldable and castable articles which can later be examined by NMR methods for defects in the interior of the material, for example vehicle tires which can withstand high stresses, or sealing material, etc.

DRAWING

Examples illustrating the invention are in part shown in the drawing and are described in more detail in the following description.

In the drawing:

FIG. 1 a set of measured curves: signal strength over various T1 values with various percentages by weight of neodymium phosphate particles as contrast-enhancing substance in MRT measurement.

DESCRIPTION OF THE EXAMPLES

A significant aspect of the invention which illustrates the advantages of the invention, especially in respect of improved MRT diagnostics or ability to be examined by NMR in general, will be described below.

Nanoparticles typically have from 10 to 1000 atoms and their size is thus in the boundary region between individual molecules and macroscopic solids. Nanoparticles can be prepared, in particular, in solutions.

FIG. 1 shows the signal intensities in water in an MRT diagnosis for various T1 values varied along the X axis (TR=response times in msec). The circles indicate the signal intensity without addition of contrast agent, and the triangles represent the signal intensity with addition of a contrast agent comprising 0.001% by weight of neodymium phosphate nanoparticles which have been prepared according to the invention. The lozenge symbols indicate the intensity at a percentage by weight of 0.01%, the squares indicate the signal intensity as a percentage by weight of 0.1% and the crosses indicate the signal intensity as a percentage by weight of 1%. As can seen from a comparison over various T1 values, the 1% addition gives an increase of from 100 to 200% over the entire TR1 range. It can likewise been seen from the drawing that even a very small addition of 0.001% by weight produces a considerable increase in the signal intensity of more than 20% in each case.

Even higher signal enhancement can be achieved when using gadolinium phosphate nanoparticles. A series of preparative methods for compounds selected for the purposes of illustration are disclosed below. It may be remarked that the scope of the present invention is not restricted to those substances, or the use of these according to the invention, whose preparation is described explicitly below. Rather, success according to the invention can be achieved by systematic variation of the composition of nanoparticles according to the invention containing metal ions which are paramagnetic, in particular particles comprising rare earth elements, together with the following list of "counterions" which together form a crystal structure which satisfies the advantageous criteria mentioned above:

Counterions which can be used are borates, aluminates, gallates, silicates, germanates, phosphates, halophosphates, oxides, arsenates, vanadates, niobates, tantalates, sulfates, tungstates, molybdates, halides and nitrides.

Selected preparative methods for various types of nanoparticles are disclosed below by way of example:

1. Synthesis of GdPO4 Nanoparticles

Prior to the actual synthesis, 1.176 g (12 mmol) of H3PO4 are admixed with 7.5 ml of tetraglyme (tetraethylene glycol dimethyl ether) and stirred in a closed vessel for 12 hours until a clear solution has been formed.

3.71 g (10 mmol) of GdC13.6H2O are subsequently dissolved in about 6 ml of MeOH.

The dissolved salt is then placed in a 250 ml flask and admixed with 100 ml of trisethylhexyl phosphate. The MeOH is then carefully taken off at RT under reduced pressure. The water of crystallization is subsequently distilled off at 30° C. under reduced pressure until the solution no longer forms any bubbles. Nitrogen (N2) is subsequently admitted into the flask and 15.7 ml (36 mmol) of trioctylamine are added to this solution. All of the phosphoric acid/tetraglyme mixture is subsequently added, the apparatus is closed and heated under nitrogen at 473 kelvin for about 40 hours.

Work-up:

Admix the cooled solution with methanol, centrifuge and decant. Wash the precipitate carefully with AR methanol, dry (no high temperatures) and weigh.

2. Synthesis of $GdTaO_4$ Colloid:

Method of Preparing $K_8Ta_6O_{19}.16H_2O$ (MW=1990.07 g/mol): Preheat a thermos to 773 K Place 25 g of KOH and 5 g of $Ta_2O_5$ in a silver crucible and heat covered (Ag foil) in the thermos for 30 minutes (until the melt is clear!). Meanwhile, heat 500 ml of distilled water to boiling. Take the crucible from the thermos, allow it to cool, and letch the solidified melt a number of times with a little hot water (total of about 50-100 ml, if sufficient). Place the solution obtained in a PE bottle (not glass!). Filter the solution through a fluted filter paper and plastic funnel into a PE bottle. To precipitate the product, admix the solution with from 1 to 4 times its volume of ethanol (technical-grade is satisfactory). Decant off the supernatant solution, if necessary after centrifugation. Dissolve the precipitate twice in about 0.1 M KOH and precipitate with ethanol. Dry on filter paper in a dissector (silica gel) and put in a bottle. (100% yield=7.5 g not achievable because of $KTaO_3$ formation).

Procedure for $GdTaO_4$:

Dissolve 2.116 g (5 mmol) of $Gd(NO_3)_3.5H_2O$ in 20 ml of water and add to 14 ml of 1 M KOH in a Teflon autoclave vessel. Dissolve 1.66 g of $K_8Ta_6O_{19}.16H_2O$ (5 mmol of Ta) and 1 ml 1 M KOH in 35 ml of water and add to the lanthanide solution. Heat the solution at 543 K for 1 hour in an autoclave (Teflon vessel) while stirring. Filter off the precipitate and stir in 200 ml of $0.5HNO_3$ (pH 0.3) which has been admixed with 6.87 g of Dequest 2010 solution (60% strength) (20 nmol). Subsequently bring to a pH of 12.5 using greater than 1 M KOH (at 1 M, about 80-200 ml!), stir overnight and centrifuge at 4500 rpm for 10 minutes. Pour off all of the supernatant liquid and discard.

Stir up the precipitate in 40 ml of water and disperse in an ultrasonic bath for 2 minutes. Subsequently centrifuge at 4500 rpm for 15 minutes and decant (peptization ?). Siphon off the supernatant liquid. Repeat the stirring up and centrifuging of the precipitate another 3 times. Subsequently wash with distilled water until peptization (=small particles redissolved) starts to occur. Centrifuge the colloidal solution at 12 000 g for 60 minutes and separate the precipitate of the nanoparticles from the supernatant liquid by decantation.

3. Synthesis of $GdVO_4$ Colloids:

Procedure for $GdVO_4$

Dissolve 4.333 g (9.5 mmol) of $Gd(NO_3)_3.5H_2O$ in 20 ml of water and add to 15 ml of 1 M NaOH in a Teflon autoclave vessel. Dissolve 1.820 g of $Na_3VO_4.10H_2O$ (5 mmol) in 35 ml of water and add to the lanthanide solution. Heat the solution at 543 K for 1 hour in an autoclave (Teflon vessel) while stirring. Filter off the precipitate and stir in 100 ml of 0.5 M $HNO_3$ which has been admixed with 6.87 g of Dequest 2010 solution (60% strength) (Monsanto) (20 mmol) for 60 minutes. Then bring to pH 5 using 1 M NaOH (about. 40-100 ml!) and centrifuge off the precipitate at 4500 rpm for 15 minutes. Subsequently wash with distilled water until peptization (=small particles redissolved) starts to occur. Centrifuge the colloidal solution at 12 000 g for 60 minutes and separate the precipitate of the nanoparticles from the supernatant liquid by decantation.

4. Synthesis of $Gd_3Ga_5O_{12}$ Nanoparticles:

Dissolve 3.89 g (10.4 mmol) of $Ga(NO_3)_3.6H_2O$, 2.68 g (5.9375 mmol) of $Gd(NO_3)_3.6H_2O$ in 20 ml of water with stirring. Pour this solution all at once into a solution of 10 ml of 25% strength of aqueous ammonia in 40 ml of water (not vice versa!). The pH has to be greater than 10, otherwise add more conc. ammonia. Centrifuge off the precipitate, subsequently decant. Stir up the precipitate 5 times in 50-100 ml of water and subsequently 5 times in 50-100 ml of methanol, wash, centrifuge and decant. Introduce the decanted but still methanol-moist precipitate together with 100 ml of molten 1,6-hexandiol into a reflux apparatus. Heat at 373 K under reduced pressure until all methanol and water has been distilled off. Admit inert gas (e.g. nitrogen or argon) and reflux for 16 hours under a stream of inert gas. Allow the mixture to cool and transfer into a glass vessel for the autoclave. Place the glass vessel in the autoclave and close loosely with a glass cap. To aid heat transfer, introduce 50 ml of 1,6-hexandiol into the space between the autoclave wall and the glass vessel. Subsequently close the autoclave, carefully evacuate twice and fill with nitrogen or argon (or another noble gas) each time. Finally, heat the autoclave to 573 K and maintain at this temperature for 4 hours. Allow the autoclave to cool, then dissolve the contents of the glass vessel in 100-250 ml of isopropanol. Centrifuge off the precipitate and wash a number of times with isopropanol. Subsequently wash with distilled water until peptization (=small particles redissolved) starts to occur. Centrifuge the colloidal solution at 12 000 g for 60 minutes and separate the precipitate of the $Gd_3Ga_5O_{12}$: Tb nanoparticles from the supernatant liquid by decantation.

The reaction can also be carried out successfully using 14-butandiol instead of 1,6-hexandiol, but the yield of small particles becomes poorer.

5. Synthesis of $Y_3Al_5O_{12}$: Nd Nanoparticles:

Transfer 4.26 g (20.8 mmol) of aluminum isopropoxide, 4.15 g (11 875 mmol) of yttrium acetate.$4H_2O$ and 215 mg (0.625 mmol) of neodymium(III) acetate.$1.5H_2O$ together with 100 ml 1,6-hexandiol into a glass vessel for the autoclave. Place the glass vessel in the autoclave and close loosely with a glass cap. To aid heat transfer, introduce 50 ml of 1,6-hexandiol into the space between the autoclave wall and the glass vessel. Subsequently close the autoclave, carefully evacuate twice and in each case fill with nitrogen or argon (or another noble gas). Finally heat the autoclave to 573 K and maintain at this temperature for 4 hours. Allow the autoclave to cool, vent the superatmospheric pressure, and only then open. Dissolve the contents of the glass vessel in 100-250 ml of isopropanol. Centrifuge off the precipitate and wash a number of times with isopropanol. Subsequently wash with distilled water until peptization (=small particles redissolved) starts to occur. Centrifuge the colloidal solution at 12 000 g for 60 minutes and separate the precipitate of the $Y_3Al_5O_{12}$: Nd nanoparticles from the supernatant liquid by decantation.

The reaction can also be carried out successfully using 1,4-butandiol instead of 1,6-hexandiol, but the yield of small particles becomes poorer.

End of the explicit preparative examples.

After transfer into the carrier liquid, the nanoparticles of the invention can be passed to their application, for instance by swallowing or intravenous injection.

Furthermore, the nanoparticles of the invention can also be homogeneously dispersed in products which later have to be carefully examined for inhomogeneities in the material in order to ensure absolutely reliable functioning of the product, e.g. for use in spaceflight, aircraft construction and high-speed tires for Formula 1 cars or aircraft.

Such a method of producing articles which can be tested nondestructively and can be produced by a shaping, in particular casting, process then comprises the following main steps:

a. Providing a liquid material suitable for NMR which contains a component having an unpaired electron, cf. description in the prior art section above, in a prescribed amount, e.g. 500 liters of liquid polymer, b. Providing a prescribed amount of carrier liquid, e.g. 1 liter of solvent suitable for the polymer and having a prescribed concentration of nanoparticles, e.g. 5% by weight of GdPO4 nanoparticles predominantly having a small size of about 5 nanometers +/− 10%, c. Mixing carrier liquid and liquid material, preferably until the nanoparticles are homogeneously dispersed in the liquid material, and d. Molding/casting the article.

The article produced can then advantageously be thoroughly examined and "looked through" using an NMR-based technique. Inhomogeneities in the entire material then show up. In this way, inclusions of air, fine hairline cracks, etc., can be reliably detected and the product is then preferably not subjected to the intended use. This increases safety in later use, because only products of very quality are used.

Although the present invention has been described above with the aid of a preferred example, it is not restricted thereto but can be modified in a wide variety of ways.

As a person skilled in the relevant field of the invention will readily see, many of the abovementioned preparative methods can be modified in a wide variety of ways in order to synthesize nanoparticles, in particular paramagnetic nanoparticles, using other constituents. Preference is in this case given to modifying the starting materials. Thus, for instance, the cationic components can be varied by using praseodymium (PR), neodymium (Nd), samarium (Sm), europium (Eu), Terbium (Tb) or gadolinium (Gd) (where not present before).

The anionic components can also be varied analogously on the basis of the abovementioned list of choices in order to obtain different materials. With few exceptions, the cationic components can be combined freely with the anionic components, as is known to a person skilled in the art from the wider field of chemistry.

Apart from the cost advantages which result from a saving of materials and can be achieved as a result of increased contrast enhancement given by a contrast agent according to the invention, the technically less demanding preparation of nanoparticles also gives an economically significant cost advantage in the production of the contrast agent according to the invention.

A further aspect of importance, especially for medical use, is the possibility of making simultaneous use of various contrast-enhancing elements which are known to have different contrasts and accumulation properties, or for which such properties will become known in the future. Due to the stable incorporation of the ions in a crystal lattice, it now becomes possible to use various elements which have hitherto not been available for use in medical diagnostics because of their toxicity.

It is also possible, depending on the choice of the cationic component, for fluorescence properties to be obtained in the compound synthesized in addition to the paramagnetic properties which are the primary subject matter of the present invention. This applies especially to the cationic components Eu, Tb, Sm, Nd, erbium (Er) and dysprosium (Dy).

The invention claimed is:

1. A method for the diagnostic examination of a patient comprising the steps of:
    a) incorporating into a carrier paramagnetic nanoparticles having a lattice structure comprising anionic and cationic components, the cationic component comprising gadolinium ions, and the anionic component selected from borates, aluminates, gallates, silicates, germinates, phosphates, halophosphates, arsenates, vanadates, niobates, tantalates, sulfates, tungstates, molybdates, halides and nitrides, wherein the nanoparticles have a size of 1 to 20 nm with a standard deviation of less than 30%,
    b) administering said carrier comprising said paramagnetic nanoparticles to a patient, orally or by intravenous injection, and
    c) subjecting the patient to an NMR-based examination.

2. The method according to claim 1, wherein said nanoparticles function as contrast agents or alter the relaxation time of a biological tissue to be examined in said patient.

3. The method according to claim 1, wherein said carrier is a liquid.

4. The method according to claim 1, wherein said NMR-based examination is selected from magnetic resonance tomography, magnetic resonance spectroscopy, magnetic resonance angiography, cardiac magnetic resonance tomography and magnetic resonance functional imaging.

5. The method according to claim 1, wherein the anionic component is selected from phosphates and vanadates.

6. The method according to claim 1, wherein the nanoparticles have a size of 1 to 4 nm.

7. The method according to claim 1, wherein said paramagnetic nanoparticles have fluorescence properties achieved by doping with a cationic component selected from samarium, neodymium, erbium and dysprosium.

8. A method for the diagnostic in vitro examination of a material comprising the steps of:
    a) taking said material from a patient,
    b) incorporating into said material paramagnetic nanoparticles having a lattice structure comprising anionic and cationic components, the cationic component comprising gadolinium ions, and the anionic component selected from borates, aluminates, galates, silicates, germinates, phosphates, halophosphates, arsenates, vanadates, niobates, tantalates, sulfates, tungstates, molybdates, halides and nitrides, wherein the nanoparticles have a size of 1 to 20 nm with a standard deviation of less than 30%, and,
    c) subjecting said marked material to NMR-based examination.

9. The method according to claim 8, wherein said material is selected from antibodies, tissue, cancer cells and inflammatory cells.

10. The method according to claim 8, wherein the anionic component is selected from phosphates and vanadates.

11. The method according to claim 8, wherein the nanoparticles have a size of 1 to 4 nm.

12. The method according to claim 8, wherein said paramagnetic nanoparticles have fluorescence properties achieved by doping with a cationic component selected from samarium, neodymium, erbium, and dysprosium.

13. A contrast agent comprising paramagnetic nanoparticles having a lattice structure, said paramagnetic nanoparticles comprising anionic and cationic components, the cationic component comprising gadolinium, and the anionic component selected from borates, aluminates, gallates, silicates, germinates, phosphates, halophosphates, arsenates, vanadates, niobates, tantalates, sulfates, tungstates, molybdates, halides and nitrides, wherein the nanoparticles have a size of 1 to 20 nm with a standard deviation of less than 30%.

14. The contrast agent according to claim 13 wherein said nanoparticles are dispersed in a liquid carrier.

15. The contrast agent according to claim 13 wherein said contrast agent is a composition for oral administration or intravenous injection.

16. The contrast agent according to claim 13 wherein the anionic component is selected from phosphates and vanadates.

17. The contrast agent according to claim 13 wherein the nanoparticles have a size of 1 to 5 nm.

18. The contrast agent according to claim 17 wherein the nanoparticles are gadolinium phosphate nanoparticles.

19. The contrast agent according to claim 13 wherein said paramagnetic nanoparticles have in addition fluorescence properties achieved by doping with another cationic component.

* * * * *